US005696140A

United States Patent [19]
Bramm et al.

[11] Patent Number: 5,696,140
[45] Date of Patent: *Dec. 9, 1997

[54] N-CYANO-N'-PYRIDYLGUANIDINES AS SEROTONIN ANTAGONISTS

[75] Inventors: Erik Bramm, Rødovre; Hans Jørgen Petersen, Frederiksberg, both of Denmark

[73] Assignee: Leo Pharmaceutical Products Ltd., Ballerup, Denmark

[*] Notice: The term of this patent shall not extend beyond the expiration date of Pat. No. 5,563,160.

[21] Appl. No.: 723,644

[22] Filed: Oct. 3, 1996

Related U.S. Application Data

[63] Continuation-in-part of Ser. No. 397,266, Mar. 15, 1995, Pat. No. 5,563,160.

[30] Foreign Application Priority Data

Sep. 15, 1992 [GB] United Kingdom ............... 9219472

[51] Int. Cl.$^6$ .................... C07D 213/75; A61K 31/44
[52] U.S. Cl. .................... 514/353; 514/344; 514/349; 546/286; 546/287; 546/288; 546/289; 546/294; 546/296; 546/297; 546/306
[58] Field of Search .................... 546/286, 287, 288, 289, 294, 296, 297, 306; 514/353, 344, 349

[56] References Cited

U.S. PATENT DOCUMENTS 5,563,160 10/1996 Bramm et al. .................... 514/353

*Primary Examiner*—Zinna Northington Davis
*Attorney, Agent, or Firm*—Cushman Darby & Cushman IP Group Pillsbury Madison & Sutro LLP

[57] ABSTRACT

The present invention relates to hitherto unknown compounds of formula or their tautomeric forms, the attachment to the pyridine ring being in the 3- or 4-position, in which R', R" are the same or different and stand for hydrogen, halogen, or trifluoromethyl, hydroxy, $C_1$–$C_4$ alkyl or alkoxy, nitro, or cyano groups. Alkylene stands for a straight or branched $C_1$–$C_8$ carbon chain, which may be substituted by hydroxy or halogen, nitro or cyano groups. X stands for oxygen, for —$S(O)_n$— where n stands for an integer from 0 to 2, or for

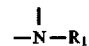

where $R_1$ is hydrogen or $C_1$–$C_4$ alkyl. R stands for hydrogen or for one or more $C_1$–$C_4$ alkyl or alkoxy, hydroxy, halogen, trifluoromethyl, cyano, carboxamido, sulfamoyl or nitro radicals. The present compounds are of value in the human and veterinary practice for treating asthma, allergy, CNS disorders, or cancer.

8 Claims, No Drawings

N-CYANO-N'-PYRIDYLGUANIDINES AS SEROTONIN ANTAGONISTS

This is a continuation-in-part of National application Ser. No. 08/397,266 filed Mar. 15, 1995, now U.S. Pat. No. 5,563,160.

The present invention relates to a series of compounds, their pharmaceutically acceptable salts, and their N-oxides, to methods for preparing the said compounds, salts or N-oxides, to pharmaceutical compositions containing said compounds, to dosage units of the compositions, and to methods of treating patients, using said compositions and dosage units.

The new compounds, which are useful in the human and veterinary therapy, have the general formula (I)

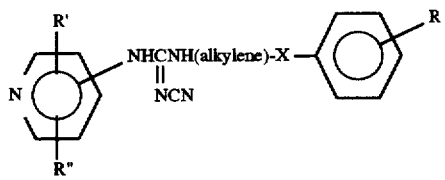

or their tautomeric forms, the attachment to the pyridine ring being in the 3- or 4-position, in which R',R" are the same or different and stand for hydrogen, halogen, or trifluoromethyl, hydroxy, $C_1$–$C_4$ alkyl or alkoxy, nitro, or cyano groups. Alkylene stands for a straight or branched $C_1$–$C_8$ carbon chain, which may be substituted by hydroxy or halogen, nitro or cyano groups. X stands for oxygen, for —S(O)$_n$— where n stands for an integer from 0 to 2, or for =N—R$_1$ where R$_1$ is hydrogen or $C_1$–$C_4$ alkyl. R stands for hydrogen or for one or more $C_1$–$C_4$ alkyl or alkoxy, hydroxy, halogen, trifluoromethyl, cyano, carboxamido, sulfamoyl or nitro radicals.

In the case where the present compounds contain one or more asymmetric carbon atoms, these compounds may form optical isomers or diastereoisomers. The present invention also comprises such isomers, and mixtures of same.

Pharmaceutically acceptable salts of compounds of formula I include hydrochlorides, hydrobromides, phosphates, sulfates, nitrates, arylsulphonates, citrates, tartrates, maleates, these examples being considered as non-limiting for the invention.

Among the preferred compounds of the invention are those of formula I, in which the attachment to the pyridine ring is in the 4-position, and/or in which alkylene stands for a straight $C_3$–$C_6$ carbon chain, and/or in which X stands for oxygen.

N-alkyl-N'-cyano-N"-pyridylguanidines, described in United Kingdom Patent No. 1,489,879, are potent potassium channel activators with a pronounced effect as pre-capillary vasodilators, reducing the total peripheral resistance in animals and in man, and are thus useful as antihypertensives. The introduction of aryloxy-containing radicals into the aliphatic groups from the cited patent has led to structures showing more specific pharmacological effects on isolated tissues and cells and with no or a negligible effect on $^{86}$Rb-efflux from potassium channels, as compared with the established effect of compounds covered by the above-mentioned U.K. Patent. Among the compounds represented by the formula (I) of the present invention, some have surprisingly proved to be serotonin (5HT) antagonists, as demonstrated in isolated rat fundus strips and in 5HT induced rat paw oedemas, making them potentially useful for treatment of diseases, in which 5HT is involved in the pathologic reaction, e.g. asthma, allergy and CNS disorders.

To study the affinity of the present compounds for serotonin$_2$ (5HT$_2$) receptors the inhibition of [$^3$H]ketanserin binding to specific 5HT$_2$ receptors in rat cortical membranes was determined by the method described in Leysen et al.: [$^3$H]Ketanserin: a selective tritiated ligand for serotonin$_2$ receptor binding sites. Molecular Pharmacology 21: 301–314 (1982). The results are shown in Table 1.

TABLE 1

5HT$_2$ receptor binding exerted by compounds of the following examples of the present invention.

| Compound from | Percent binding | | |
|---|---|---|---|
| | $10^{-9}$ M | $10^{-7}$ M | $10^{-5}$ M |
| Example No. 5 | 34.5 | 60.1 | 95.4 |
| Example No. 14 | 41.3 | 66.5 | 98.4 |
| Example No. 18 | 21.3 | 41.1 | 54.2 |

These results show that the compounds of the present invention inhibit the binding of ketanserin to 5HT$_2$ receptors and therefore have high affinity for such receptors.

Some members of the present class also inhibit the proliferation of tumour cells in culture and prolong the survival of tumour-bearing rats, thus making them potentially useful in antineoplastic chemotherapy.

The inhibition of tumour cell proliferation was studied using Yoshida sarcoma cells, originally derived from rat hepatic tumours induced by the carcinogen o-aminoazotoluene. The cells were cultured in vitro for 24 hours in the presence of the compound under investigation. DNA synthesis was measured by incorporation of [$^3$H] thymidine, and the median inhibitory concentrations (IC$_{50}$) of the compounds were calculated. The cytotoxicity of the compounds in normal lymphocytes was assessed by the dye exclusion method and expressed as the concentrations resulting in 50% viability (VC$_{50}$). Results are shown in Table 2.

TABLE 2

Inhibition of tumour cell proliferation and effect on cell viability in vitro by compounds of the following examples of the present invention.

| Compound from | Inhibition of tumour cell proliferation IC$_{50}$ (μM) | Effect on viability of normal cells VC$_{50}$ (μM) |
|---|---|---|
| Example No. 5 | 3.3 | >100 |
| Example No. 14 | 0.17 | 100 |
| Example No. 18 | 0.75 | >100 |

The results show that the compounds of the present invention are able to inhibit the proliferation of tumour cells in vitro at concentrations that are approximately 100 times lower than those that are cytotoxic to normal cells.

Similarly, promising in vitro results were obtained, when using a variety of human cancer cell lines as shown in Table 3.

TABLE 3

Inhibition of tumour cell proliferation in vitro in human small cell lung carcinoma (NYH) and human breast cancer (MCF-7) cell lines by compounds of the following examples of the present invention.

| Compound from | NYH $IC_{50}$ (nM) | MCF-7 $IC_{50}$ (nM) |
|---|---|---|
| Example No. 33 | 0.58 | 6.2 |
| Example No. 54 | 0.59 | 1.4 |
| Example No. 43 | 1.9 | 21 |
| Example No. 52 | 1.4 | 4.3 |
| Example No. 53 | 0.52 | 0.74 |

The prolongation of survival time of tumour-bearing rats was studied in LEW/Mol inbred female rats inoculated with Yoshida sarcoma cells (identical to the cells described above) in a number of $2 \times 10^7$ cells. Tumour-bearing rats were dosed orally once daily from day 3 after the transfer of tumour cells and until death or until the body-weights had increased by 10% as a consequence of tumour proliferation. The time for death of 50% of the animals was calculated by linear regression analysis. Results are shown in Table 4.

TABLE 4

Survival of Yoshida tumour-bearing rats treated with some compounds of the following examples of the present invention.

| Treatment | Compound | Dose (mg/kg, p.o.) | Time to 50% of animals dead of cancer |
|---|---|---|---|
| None | — | — | 7.5 days |
| Reference compounds (known antineoplastics) | Cyclo-phosphamide | 0.3 | 19.1 days |
| | 6-Mercapto-purine | 10 | 12.2 days |
| Compounds from the present invention | Example No. 5 | 10 | 12.0 days |
| | | 20 | 15.5 days |
| | | 50 | a |
| | | 100 | a |
| | Example No. 14 | 20 | 10.8 days |
| | Example No. 18 | 20 | 11.0 days | a No rats had died on day 14. Calculation of 50% dead not possible.

These results show that the compounds of the present invention are able to prolong the survival time of Yoshida sarcoma tumour-bearing rats.

In addition the antitumour effect of the compounds of the present invention was determined in nude mice carrying a human small cell lung carcinoma (NYH).

Nude mice were inoculated subcutaneously with a 0.2 ml NYH cell suspension ($5 \times 10^7$ cells/ml). Two weeks after inoculum animals were divided in treatment and control groups. All mice were dosed p.o. once daily according to group from day 14 to 28.

In this model the therapeutic response was determined as exemplified using compound from Example No. 43 (Table 5)

TABLE 5

Therapeutic antitumour effect of the compound of Example No. 43 in nude mice carrying a human small cell lung carcinoma (NYH).

| Day | Untreated mice tumour areas ($mm^2$) | Vehicle treated tumour areas ($mm^2$) | Ex. No. 43 50 mg/kg tumour areas ($mm^2$) | Ex. No. 43 25 mg/kg tumour areas ($mm^2$) |
|---|---|---|---|---|
| 11 | 13–45[a]/3[b] | 26–101[a]/6[b] | 17–64[a]/6[b] | 12–36[a]/6[b] |
| 14 | 10–49/7 | 7–170/8 | 16–131/10 | 23–58/8 |
| 18 | 10–95/8 | 13–332/9 | 8–109/10[c] | 12–59/8[c] |
| 21 | 28–244/8 | 11–383/10 | 6–40/5[c] | 11–18/5[c] |
| 25 | 50–262/8 | 18–531/10 | 3–27/5[c] | 4–14/3[c] |
| 28 | 104–500/8 | 31–398/9 | 0—0/0[c] | 0—0/0[c] |

[a]Range
[b]Number of tumours
[c]Significantly different from untreated or vehicle treated mice, Mann-Whitney's U-test p < 0.05

This experiment confirms in vivo in a therapeutic experiment on well established tumours in nude mice the potent effect of the compound of the present invention on the NYH human small cell carcinoma.

The 5HT antagonistic effect of the compounds of the invention may confer desirable anti-emetic effects to offset the known emetic effects of other antineoplastic drugs that may be used in combination with compounds of the present invention.

The compounds of the invention are well tolerated and non-toxic and are exerting the described beneficial activities with no or minimal effect on the systemic blood pressure. In general, they may be administered by oral, intravenous, intraperitoneal, intranasal or transdermal routes.

The present invention also relates to methods for preparing the desired compounds of formula (I).

In one embodiment a pyridylcarbodiimide of the formula (II)

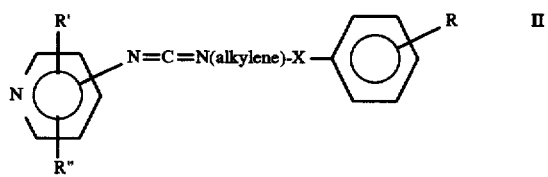

in which the substituents are as defined above in (I), is reacted with an equivalent or an excess of cyanamide with or without use of ordinary, inert solvent, at or about room temperature. The reaction may be catalyzed by bases, such as triethylamine.

In another embodiment a thiourea of the formula

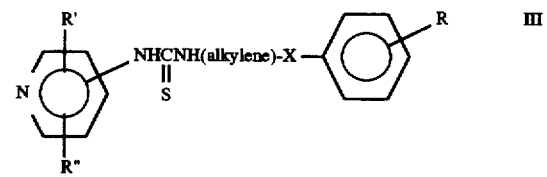

in which the substituents are as defined above in (I), is reacted with one or more equivalents of N,N'-dicyclohexylcarbodiimide (DCCD) and of cyanamide in an inert solvent, such as acetonitrile, at or above room temperature, yielding a compound of formula (I) and N,N'-dicyclohexylthiourea (DCTU). A basic catalyst, e.g. triethylamine, may be used.

In still another embodiment a compound of formula (IV)

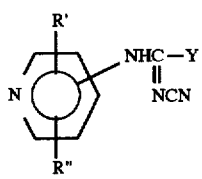

in which the substituents R' and R" are as defined above, and where Y is halogen, preferably chlorine, or a $C_1$–$C_4$ alkylthio radical, is reacted with the appropriate amine,

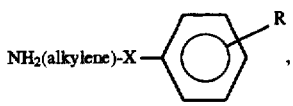

where the symbols have the same meaning as in formula (I). The amine may be used in an excess in an inert solvent, e.g. pyridine, at or above room temperature, e.g. in boiling pyridine. In the case where Y stands for halogen it may be preferable to use an equivalent of an acid binding agent, e.g. a tertiary amine.

In still another embodiment a compound of the formula (V)

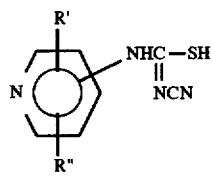

in which the substituents are as defined above, is reacted with an equivalent, or a slight excess of the requisite amine,

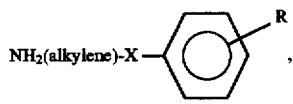

where the symbols have the same meaning as in formula (I), in the presence of one equivalent, or slightly more, of DCCD, in an inert solvent, such as dimethylformamide at 0° C. or at room temperature, resulting in the formation of (I) and DCTU.

In the methods described above a stereoisomer of (I) may be obtained, if desired, by using the corresponding isomer of the respective amine,

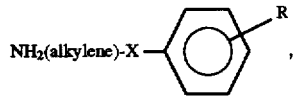

where the symbols have the same meaning as in formula (I), as the starting material. Alternatively, a racemic starting material may be used, whereupon the resulting mixture may be subjected to a racemate resolution, e.g. by crystallization of a suitable salt with an optically active acid in known manner, or by chromatography on an asymmetric column.

The compounds of formula (II) may be prepared from the requisite thioureas (III) or corresponding ureas by conventional methods, e.g. by treating with triphenylphosphine, carbon tetrachloride and triethylamine in dry methylene chloride.

Compounds of formula (IV) may be obtained by reacting cyanamide with the appropriate pyridylisothiocyanate in the presence of a tertiary amine, followed by treatment with a $C_1$–$C_4$ alkyl iodide, in the case where Y stands for a $C_1$–$C_4$ alkylthio radical. Where Y stands for halogen, compounds (IV) may be obtained by reacting a compound of formula (V) with e.g. phosgene, in an inert solvent, in the presence of a tertiary amine.

The starting materials of formula (V) can be prepared from the requisite pyridylisothiocyanates and cyanamide, using one equivalent of a tertiary amine, in an inert solvent. Alternatively, a pyridyldithiocarbamic acid, e.g. 4-pyridyldithiocarbamic acid[1], may be reacted with at least two equivalents of cyanamide and one equivalent of a tertiary amine in e.g. methanol, to yield the amine salt of the desired pyridylcyaniminothiocarbamic acid (V).

The N- and S-oxides of formula (I) may conveniently be prepared by oxidation of the parent compounds with e.g. m-chloroperbenzoic acid in an inert solvent, e.g. chloroform.

[1] Synth. Comm. 14 1275 (1984)

It is further an object of the present invention to provide pharmaceutical compositions of (I) which are useful in the treatment of the above mentioned diseases.

The amount required of a compound of formula (I) (hereinafter referred to as the active ingredient) for therapeutic effect will, of course, vary both with the particular compound, the route of administration and the mammal under treatment. A suitable dose of a compound of formula (I) for systemic treatment is 0.1 to 400 mg per kilogram bodyweight, the most preferred dosage being 1.0 to 100 mg per kg of mammal bodyweight, for example 5 to 20 mg/kg; administered once or more times daily.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include those in a form suitable for oral, rectal, parenteral (including subcutaneous, intramuscular, intravenous and intraperitoneal) administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredient. Compressed tablets may be prepared by compressing, in a suitable machine, the active ingredient in a free-flowing form, such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including anti-oxidants), emulsifying agents and the like.

The compositions may further contain other therapeutically active compounds usually applied in the treatment of the above-mentioned pathological conditions, e.g. anti-asthmatics and antineoplastic agents which may result in synergistic effects on tumour cells.

According to the invention, the present compounds are administered to a patient suffering from one of the above mentioned pathological conditions in a daily dose (for adults) from 7 mg to 28000 mg, preferably from 70–7000 mg, and in the veterinary practice correspondingly in daily doses from 0.1 to 400 mg/kg bodyweight.

The invention will now be further described in the following non-limiting Examples:

EXAMPLE 1

N-Cyano-N'-(3-phenoxypropyl)-N"-3-pyridylquanidine

N-(3-Phenoxypropyl)-N'-3-pyridylthiourea (1.73 g) was suspended in acetonitrile (10 ml), and cyanamide (0.50 g) and N,N"-dicyclohexylcarbodiimide (2.47 g) were added, followed by triethylamine (0.14 ml). The mixture was kept with stirring at room temperature for 3 days, when it was filtered, washed with acetonitrile and with ether to leave a solid mixture of the crude product and N,N'-dicyclohexylthiourea, which was removed by extraction with chloroform (25 ml). The product was collected by filtration and washed with chloroform.

It was further purified by dissolving the obtained residue in 0.5N hydrochloric acid (20 ml), filtering, and re-precipitating with 9N sodium hydroxide.

Mp. 185°–187° C.

$^1$H NMR (DMSO) δ: 1.99 (m, 2H), 3.42 (m, 2H), 4.02 (t, 2H), 6.93 (m, 3H), 7.27 (m, 2H), 7.36 (dd, 1H), 7.51 (bt, 1H), 7.67 (m, 1H), 8.34 (m, 1H), 8.47 (m, 1H), 9,15 (bs, 1H).

EXAMPLE 2

N-Cyano-N'-(2-phenylaminoethyl)-N"-4-pyridylquanidine

N-Cyano-N'-4-pyridylthiourea (1.80 g) was suspended in dimethylformamide (5 ml). While stirring in an ice bath N-phenylethylenediamine (1.4 ml) and N,N'-dicyclohexylcarbodiimide (2.50 g) were added, resulting in a clear solution. The mixture was left at room temperature for 3 days, when the suspension formed was evaporated extensively under high vacuum. The residue was triturated repeatedly with ether (15 ml portions), and the residual solid was extracted with 1N hydrochloric acid (50 ml). After filtration, the crude product was precipitated from the filtrate by addition of 9N sodium hydroxide and taken up into ethyl acetate (3×75 ml).

After evaporation of the combined ethyl acetate extracts the residue was stirred with a 1:1 mixture of acetone-ether to yield the pure compound.

Mp. 167°–170° C.

$^1$H NMR (DMSO) δ: 3.23 (m, 2H), 3.44 (m, 2H), 5.72 (bt, 1H), 6.54 (t, 1H), 6.60 (d, 2H), 7.08 (dd, 2H), 7.21 (d, 2H), 7.86 (bs, 1H), 8.37 (m, 2H), 9.48 (bs, 1H).

EXAMPLE 3

N-Cyano-N'-(1-phenoxy-2-propyl)-N"-4-pyridylquanidine

N-(1-Phenoxy-2-propyl)-N'-4-pyridylcarbodiimide (2.53 g) was dissolved in ether (5 ml). Cyanamide (0.55 g) and triethylamine (0.04 ml) were added, and the mixture was left with stirring overnight in an open flask at room temperature.

The solidified residue was stirred with ether (20 ml), and the suspension was filtered and washed with ether to yield the crude product, which was dissolved in 0.5N hydrochloric acid (30 ml), filtered and re-precipitated by addition of 9N sodium hydroxide, then collected by filtration and washed with water to afford the pure compound.

Mp. 164°–166° C.

$^1$H NMR (DMSO) δ: 1.24 (d, 3H), 4.01 (d, 2H), 4.31 (m, 1H), 6.97 (m, 3H), 7.20 (bs, 2H), 7.31 (dd, 2H), 7.96 (bd, 1H), 8.35 (bs, 2H), 9.58 (bs, 1H).

EXAMPLE 4

N-Cyano-N'-(2-phenylthioethyl)-N"-3-pyridylquanidine

S-Methyl N-cyano-N'-3-pyridylisothiourea (1.92 g) was dissolved in pyridine (10 ml), and 2-phenylthioethylamine (3.06 g) was added. The mixture was kept at room temperature for 4 days, when it was evaporated in vacuo. The residue was triturated with ether (40 ml), and the resulting suspension was filtered and washed with ether.

The crude product was purified by dissolving in excess 0.5N hydrochloric acid, filtering and precipitating by addition of 9N sodium hydroxide to the aqueous filtrate.

Mp. 126°–128° C.

$^1$H NMR (DMSO) δ: 3.14 (m, 2H), 3.42 (m, 2H), 7.20 (m, 1H), 7.35 (m, 5H), 7.57 (bt, 1H), 7.67 (m, 1H), 8.36 (m, 1H), 8.47 (m, 1H), 9.25 (bs, 1H).

EXAMPLE 5

N-Cyano-N'-(3-phenoxypropyl)-N"-4-pyridylquanidine

By following the procedure of Example 1, but substituting N-(3-phenoxypropyl)-N'-4-pyridylthiourea for N-(3-phenoxypropyl)-N'-3-pyridylthiourea, the desired compound was obtained.

$^1$H NMR (DMSO) δ: 2.00 (m, 2H), 3.45 (q, 2H), 4.03 (t, 2H), 6.93 (m, 3H), 7.21 (bd, 2H), 7.28 (m, 2H), 7.91 (bt, 1H), 8.37 (bd, 2H), 9.43 (very b, 1H).

EXAMPLE 6

N-Cyano-N'-(2-phenoxyethyl)-N"-3-pyridylquanidine

By following the procedure of Example 1, but substituting N-(2-phenoxyethyl)-N'-3-pyridylthiourea for N-(3- phenoxypropyl)-N'-3-pyridylthiourea, the desired compound was obtained.

Mp. 182°–184° C.

$^1$H NMR (DMSO) δ: 3.62 (m, 2H), 4.11 (t, 2H), 6.96 (m, 3H), 7.31 (m, 2H), 7.37 (dd, 1H), 7.60 (bt, 1H), 7.67 (m, 1H), 8.35 (m, 1H), 8.48 (m, 1H), 9.25 (bs, 1H).

EXAMPLE 7

N-Cyano-N'-(2-phenoxyethyl)-N"-4-pyridylguanidine

By following the procedure of Example 1, but substituting N-(2-phenoxyethyl)-N'-4-pyridylthiourea for N-(3-phenoxypropyl)-N'-3-pyridylthiourea, the desired compound was obtained.

Mp. 167°–170° C.

$^1$H NMR (DMSO) δ: 3.67 (m, 2H), 4.13 (t, 2H), 6.95 (m, 3H), 7.24 (m, 2H), 7.30 (dd, 2H), 8.04 (bs, 1H), 8.38 (m, 2H), 9.55 (bs, 1H).

EXAMPLE 8

N-Cyano-N'-(1-phenoxy-2-propyl)-N"-3-pyridylguanidine

By following the procedure of Example 1, but substituting N-(1-phenoxy-2-propyl)-N'-3-pyridylthiourea for N-(3-phenoxypropyl)-N'-3-pyridylthiourea, the desired compound was obtained.

Mp. 130°–133° C.

$^1$H NMR (DMSO) δ: 1.23 (d, 3H), 3.98 (m, 2H), 4.29 (m, 1H), 6.97 (m, 3H), 7.30 (m, 2H), 7.34 (dd, 1H), 7.45 (bd, 1H), 7.65 (m, 1H), 8.31 (m, 1H), 8.46 (m, 1H), 9.25 (bs, 1H).

EXAMPLE 9

N-Cyano-N'-(2-phenylthioethyl)-N"-4-pyridylguanidine

By following the procedure of Example 1, but substituting N-(2-phenylthioethyl)-N'-4-pyridylthiourea for N-(3-phenoxypropyl)-N'-3-pyridylthiourea, the desired compound was obtained.

Mp. 161°–163° C.

$^1$H NMR (DMSO) δ: 3.17 (m, 2H), 3.46 (m, 2H), 7.21 (m, 3H), 7.35 (m, 4H), 8.00 (bs, 1H), 8.39 (d, 2H), 9.56 (bs, 1H).

EXAMPLE 10

N-(3-p-Chlorophenoxy-2-hydroxypropyl)-N'-cyano-N"-4-pyridylguanidine

By following the procedure of Example 2, but substituting 3-p-chlorophenoxy-2-hydroxypropylamine for N-phenylethylenediamine, the desired compound was obtained.

Mp. 149°–151° C.

$^1$H NMR (DMSO) δ: 3.45 (m, 3H), 3.96 (m, 3H), 6.96 (d, 2H), 7.28 (m, 4H), 7.76 (bt, 1H), 8.37 (d, 2H), 4.5–10.5 (very b, 1H).

EXAMPLE 11

N-(2-p-Chlorophenoxyethyl)-N'-cyano-N"-3-pyridylguanidine

N-(2-p-Chlorophenoxyethyl)-N'-3-pyridylthiourea (1.05 g) was suspended in acetonitrile (10 ml), and cyanamide (285 mg), N,N'-dicyclohexylcarbodiimide (1.40 g) and triethylamine (0.04 ml) were added. The mixture was kept with stirring at room temperature for a week, when it was filtered, washed with acetonitrile and with ether. The solid mixture of the crude product and N,N'-dicyclohexylthiourea was extracted with chloroform (15 ml) to leave the pure product, which was collected by filtration and washed with chloroform and ether.

Mp. 174°–176° C.

$^1$H NMR (DMSO) δ: 3.61 (bs, 2H), 4.10 (t, 2H), 7.00 (d, 2H), 7.35 (d, 2H), 7.37 (m, 1H), 7.59 (bs, 1H), 7.66 (m, 1H), 8.34 (dd, 1H), 8.47 (d, 1H), 9.25 (bs, 1H).

EXAMPLE 12

N-(2-p-Chlorophenoxyethyl)-N'-cyano-N"-4-pyridylguanidine

By following the procedure of Example 11, but substituting N-(2-p-chlorophenoxyethyl)-N'-4-pyridylthiourea for the 3-pyridyl analogue, the desired compound was obtained.

Mp. 174.5°–177° C.

$^1$H NMR (DMSO) δ: 3.66 (bt, 2H), 4.13 (t, 2H), 6.99 (d, 2H), 7.22 (bd, 2H), 7.34 (d, 2H), 8.01 (bs, 1H), 8.38 (d, 2H), 9.57 (bs, 1H).

EXAMPLE 13

N-Cyano-N'-(4-phenoxybutyl)-N"-3-pyridylguanidine

N-(4-Phenoxybutyl)-N'-3-pyridylthiourea (1.41 g) was dissolved in acetonitrile (10 ml), and cyanamide (400 mg), N,N'dicyclohexylcarbodiimide (1.95 g) and triethylamine (0.08 ml) were added. The mixture was stirred for 3 days at room temperature, when it was filtered, washed with acetonitrile, and ether to yield a solid mixture of the crude product and N,N'-dicyclohexylthiourea. The pure compound was obtained by extracting the mixture with 0.5N hydrochloric acid (16 ml), filtering and re-precipitation by addition of 9N sodium hydroxide to the filtrate.

Mp. 137.5°–138° C.

$^1$H NMR (DMSO) δ: 1.71 (m, 4H), 3.30 (q, 2H), 3.98 (t, 2H), 6.92 (m, 3H), 7.28 (m, 2H), 7.37 (dd, 1H), 7.48 (bt, 1H), 7.67 (bd, 1H), 8.34 (dd, 1H), 8.47 (d, 1H), 9.10 (bs, 1H).

EXAMPLE 14

N-Cyano-N'-(4-phenoxybutyl)-N"-4-pyridylguanidine

By following the procedure of Example 13, but substituting N-(4-phenoxybutyl)-N'-4-pyridylthiourea for the 3-pyridyl analogue, the desired compound was obtained.

Mp. 131° C.

$^1$H NMR (DMSO) δ: 1,72 (m, 4H), 3.34 (m, 2H), 3.99 (t, 2H), 6.92 (m, 3H), 7.22 (bs, 2H), 7.27 (m, 2H), 7.90 (bt, 1H), 8.38 (bd, 2H), 9.42 (bs, 1H).

EXAMPLE 15

N-(5-bromo-3-pyridyl)-N'-cyano-N"-(2-phenylthioethyl)guanidine

S-Methyl N-(5-bromo-3-pyridyl)-N'-cyanoisothiourea (650 mg) and 2-phenylthioethylamine (740 mg) in pyridine (0.5 ml) were heated to 50° C. for 5 hours. To the resulting clear solution was added ether (10 ml), and the desired pure compound was collected by filtration and washed with ether.

Mp. 168° C.

$^1$H NMR (DMSO) δ: 3.16 (t, 2H), 3.43 (bs, 2H), 7.20 (m, 1H), 7.35 (m, 4H), 7.77 (m, 1H), 7.96 (t, 1H), 8.47 (t, 2H), 9.34 (bs, 1H).

EXAMPLE 16

N-Cyano-N'-(2-phenylthioethyl)-N"-3-pyridylquanidine, S-oxide

N-Cyano-N'-(2-phenylthioethyl)-N"-3-pyridylguanidine (Example 4) (595 mg) was suspended in chloroform (40 ml) and m-chloroperbenzoic acid (520 mg) was added portionwise over 15 minutes, while stirring at 0° C.- The resulting clear solution was evaporated in vacuo, and the residue was stirred with ether (50 ml), filtered and washed with ether to afford the crude product. The pure compound was obtained by flash chromatography on a silica column, using a 90:10 mixture of methylene chloride-methanol as eluent.

Mp. 167.5° C.

$^1$H NMR (DMSO) δ: 3.00 (m, 1H), 3.24 (m, 1H), 3.45 (m, 1H), 3.58 (m, 1H), 7.39 (dd, 1H), 7.47–7.75 (m, 7H), 8.36 (dd, 1H), 8.47 (d, 1H), 9.32 (bs, 1H).

EXAMPLE 17

N-Cyano-N'-(2-phenylthioethyl)-N"-4-pyridylquanidine, S-oxide

By following the procedure of Example 16, but substituting N-cyano-N'-(2-phenylthioethyl)-N"-4-pyridylguanidine (Example 9) for the 3-pyridyl analogue, the desired compound was obtained.

Mp. 166.5°–167° C.

$^1$H NMR (DMSO) δ: 3.05 (m, 1H), 3.27 (m, 1H), 3.50 (m, 1H), 3.63 (m, 1H), 7.21 (m, 2H), 7.60 (m, 3H), 7.70 (m, 2H), 7.95 (m, 1H), 8.40 (m, 2H), 9.66 (m, 1H).

EXAMPLE 18

N-Cyano-N'-(5-phenoxypentyl)-N"-4-pyridylquanidine

By following the procedure of Example 14, but substituting N-(5-phenoxypentyl)-N'-4-pyridylthiourea for N-(4-phenoxybutyl)-N'-4-pyridylthiourea, the desired compound was obtained.

Mp. 188°–189° C.

$^1$H NMR (DMSO) δ: 1.46 (m, 2H), 1.59 (m, 2H), 1.74 (m, 2H), 3.31 (m, 2H), 3.96 (t, 2H), 6.91 (m, 3H), 7.21 (bd, 2H), 7,27 (t, 2H), 7.87 (bs, 1H), 8.38 (d, 2H), 9.42 (bs, mH).

EXAMPLE 19

N-Cyano-N'-(3-phenoxypropyl)-N"-4-pyridylquanidine, N-oxide

N-Cyano-N'-(3-phenoxypropyl)-N"-4-pyridylguanidine (Example 5) (1.20 g) was suspended in methylene chloride (20 ml), and m-chloroperbenzoic acid (990 mg) was added portionswise over 2 hours, while stirring at 0° C. The resulting solution was evaporated in vacuo, and the residue was stirred with 2 portions of ether (20 ml), which were removed by decanting. Methylene chloride (20 ml) was added, and an additional amount of m-chloroperbenzoic acid (990 mg) was introduced, portionwise over 1 hour, while stirring at 0° C. The mixture was evaporated in vacuo, and finally the residue was extracted twice with ether (20 ml) to afford the crude product. The pure compound was obtained by flash chromatography on a silica column, using a 80:20:1 mixture of methylene chloride-methanol-25% aqueous ammonia as eluent.

Mp. 165°–166° C.

$^1$H NMR (DMSO) δ: 2.00 (m, 2H), 3.50 (q, 2H), 4.03 (t, 2H), 6.92 (t, 1H), 6.93 (d, 2H), 7.27 (m, 2H), 7.45 (bd, 2H), 8.08 (t, 1H), 8.28 (d, 2H), 9.98 (bs, 1H).

EXAMPLE 20

N-(5-Bromo-3-pyridyl)-N'-cyano-N"-(3-phenoxypropyl)guanidine

By following the procedure of Example 15, but substituting 3-phenoxypropylamine for 2-phenylthioethylamine, the, the desired compound was obtained.

Mp. 129°–130° C.

$^1$H NMR (DMSO) δ: 1.98 (m, 2H), 3.42 (q, 2H), 4.01 (t, 2H), 6.92 (m, 3H), 7.28 (m, 2H), 7.68 (bt, 1H), 7.95 (t, 1H), 8.44 (d, 1H), 8.47 (d, 1H), 9.23 (bs, 1H).

EXAMPLE 21

N-Cyano-N'-(6-phenoxyhexyl)-N"-4-pyridylquanidine

By following the procedure of Example 14, but substituting N-(6-phenoxyhexyl)-N'-4-pyridylthiourea for N-(4-phenoxybutyl)-N'-4-pyridylthiourea, the desired compound was obtained.

EXAMPLE 22

Tablet

Manufacture of 10,000 tablets

| | | |
|---|---|---|
| I | N-cyano-N'-(5-phenoxypentyl)-N"-4-pyridylguanidine (active compound) | 10,000 kg |
| | Cross carmellose sodium | 0,300 kg |
| II | Hydroxypropylmethyl cellulose, low viscosity type | 0,200 kg |
| | Sorbimacrogol oleate | 0,010 kg |
| | Purified water | q.s. |
| III | Crosscarmellose sodium | 0,200 kg |
| | Coloidal anhydrous silica | 0,050 kg |
| | Magnesium stearate | 0,050 kg |

I is mixed intimately in a highshear mixer, is wetted with II and granulated into a moist mass. The moist granulate is dried in a fluid-bed dryer at an inlet air temperature of 60° C. until the dried granulate has a water activity of 0.3–0.4 (=in equilibrium with air of 30–40% R.H.).

The dried granulate is passed through a sieve with mesh openings of 850 μm.

The sieved granulate is finally mixed with III in a cone mixer.

The finished granulate is compressed into tablets of mass 1071 mg and sufficient hardness.

EXAMPLE 23

N-Cyano-N'-3-p-fluorophenoxypropyl-N"-4-pyridylquanidine

By following the procedure of Example 11, but substituting N-3-p-fluorophenoxypropyl-N'-4-pyridylthiourea for N-2-p-chlorophenoxyethyl-N'-3-Pyridylthiourea, the desired compound was obtained.

Mp. 132° C.

$^1$H NMR (DMSO) δ: 1.98 (m, 2H), 3.44 (bs, 2H), 4.00 (t, 2H), 6.94 (m, 2H), 7.11 (m, 2H), 7.20 (bd, 2H), 7.90 (bs, 1H), 8.37 (d, 2H), 9.46 (bs, 1H).

EXAMPLE 24

N-5-p-Chlorophenoxypentyl-N'-cyano-N"-4-pyridylguanidine

By following the procedure of Example 11, but substituting N-5-p-chlorophenoxypentyl-N'-4-pyridylthiourea for N-2-p-chlorophenoxyethyl-3-pyridylthiourea, the desired compound was obtained.

$^1$H NMR (DMSO) δ: 1.45 (m, 2H), 1.59 (m, 2H), 1.73 (m, 2H), 3.30 (bq, 2H), 3.96 (t, 2H), 6.94 (d, 2H), 7.21 (bd, 2H), 7.31 (d, 2H), 7.86 (bt, 1H), 8.38 (d, 2H), 9.40 (bs, 1H).

EXAMPLE 25

N-Cyano-N'-5-phenoxypentyl-N"-4-pyridylguanidine, N-oxide

By following the procedure of Example 19, but substituting the cyanoguanidine of Example 18 for N-cyano-N'-3-phenoxypropyl-N"-4-pyridylguanidine, the desired compound was obtained.

$^1$H NMR (DMSO) δ: 1.44 (m, 2H), 1.58 (m, 2H), 1.73 (m, 2H), 3.27 (q, 2H), 3.96 (t, 2H), 6.92 (m, 3H), 7.29 (m, 4H), 7.73 (t, 1H), 8.10 (d, 2H), 9.33 (bs, 1H).

EXAMPLE 26

N-5-p-Chlorophenoxypentyl-N'-cyano-N"-3-pyridylguanidine

By following the procedure of Example 4, but substituting 5-p-chlorophenoxypentylamine for 2-phenylthioethylamine, and reacting at 90° C. for 5 hours, the desired compound was obtained.

$^1$H NMR (DMSO) δ: 1.43 (m, 2H), 1.58 (m, 2H), 1.73 (m, 2H), 3.25 (bt, 2H), 3.96 (t, 2H), 6.95 (d, 2H), 7.31 (d, 2H), 7.37 (m, 1H), 7.45 (bs, 1H), 7.66 (m, 1H), 8.33 (dd, 1H), 8.46 (d, 1H), 9.03 (bs, 1H).

EXAMPLE 27

N-Cyano-N'-6-phenoxyhexyl-N"-3-pyridylguanidine

By following the procedure of Example 26, but substituting 6-phenoxyhexylamine for 5-p-chlorophenoxypentylamine, the desired compound was obtained.

$^1$H NMR (DMSO) δ: 1.25–1.48 (m, 4H), 1.54 (m, 2H), 1.72 (m, 2H), 3.23 (q, 2H), 3.95 (t, 2H), 6.90 (t, 1H), 6.91 (d, 2H), 7.27 (t, 2H), 7.37 (dd, 1H), 7.44 (bt, 1H), 7.66 (bd, 1H), 8.33 (dd, 1H), 8.46 (d 1H), 9.08 (bs, 1H).

EXAMPLE 28

N-6-D-Chlorophenoxyhexyl-N'-cyano-N"-3-pyridylguanidine

By following the procedure of Example 26, but substituting 6-p-chlorophenoxyhexylamine for 5-p-chlorophenoxypentylamine, the desired compound was obtained.

$^1$H NMR (DMSO) δ: 1.25–1.48 (m, 4H), 1.54 (m, 2H), 1.71 (m, 2H), 3.23 (bs, 2H), 3.95 (t, 2H), 6.94 (d, 2H), 7.31 (d, 2H), 7.36 (dd, 1H), 7.43 (bs, 1H), 7.66 (bd, 1H), 8.33 (dd, 1H), 8.46 (d, 1H), 9.07 (bs, 1H).

EXAMPLE 29

N-Cyano-N'-6-o-methoxyphenoxyhexyl-N"-3-pyridylguanidine

By following the procedure of Example 26, but substituting 6-o-methoxyphenoxyhexylamine for 5-p-chlorophenoxypentylamine, the desired compound was obtained.

$^1$H NMR (DMSO) δ: 1.25–1.50 (m, 4H), 1.55 (m, 2H), 1.72 (m, 2H), 3.23 (bq, 2H), 3.74 (s, 3H), 3.93 (t, 2H), 6.82–6.98 (m, 4H), 7.35 (dd, 1H), 7.43 (bt, 1H), 7.65 (bd, 1H), 8.33 (dd, 1H), 8.46 (d, 1H), 9.05 (s, 1H).

EXAMPLE 30

N-Cyano-N'-7-phenoxyheptyl-N"-3-pyridylguanidine

By following the procedure of Example 26, but substituting 7-phenoxyheptylamine for 5-p-chlorophenoxypentylamine, the desired compound was obtained.

$^1$H NMR (DMSO) δ: 1.25–1.60 (m, 8H), 1.71 (m, 2H), 3.22 (bt, 2H), 3.94 (t, 2H), 6.90 (m, 3H), 7.27 (m, 2H), 7.36 (dd, 1H), 7.43 (bt, 1H), 7.66 (m, 1H), 8.33 (dd, 1H), 8.45 (d, 1H), 9.03 (bs, 1H).

EXAMPLE 31

S-Methyl N-cyano-N'-4-pyridylisothiourea

4-Aminopyridine (7.6 g) and S,S'-dimethyl N-cyano-dithio-iminocarbonate (14.0 g) were dissolved in dimethylformamide (60 ml). While stirring at 0° C. sodium hydride (50% dispersion in mineral oil) (4.60 g) was introduced over 15 minutes. The mixture was stirred at 0° C. for 6 hours, then at room temperature overnight.

Ether (250 ml) and petroleum ether (50 ml) were added. After decanting of the supernatant phase the oily residue was stirred twice with ether:petroleum ether (5:1) (250 ml). After decantings the resulting semi-solid was treated with ice-water (150 ml) and filtered. The stirred, ice-cooled filtrate was treated with glacial acetic acid (5.6 ml), and the precipitate was collected by filtration and washed with water and small portions of ether. Recrystallization from aqueous methanol afforded the pure compound.

$^1$H NMR (DMSO) δ: 2.64 (s, 3H), 7.49 (d, 2H), 8.42 (d, 2H).

EXAMPLE 32

N-Cyano-N'-(4-phenylthiobutyl)-N"-4-pyridylguanidine

By following the procedure of Example 1, but substituting N-(4-phenylthiobutyl)-N'-4-pyridylthiourea for N-(3-phenoxypropyl)-N'-4-pyridylthiourea, the desired compound was obtained.

The compound was further purified by a recrystallisation from water/acetone.

Mp. 146° C.

$^1$H NMR (DMSO) δ: 1.63 (m, 4H), 2.99 (t, 2H), 3.29 (bt, 2H), 7.19 (m, 3H), 7.31 (m, 4H), 7.86 (bs, 1H), 8.37 (d, 2H), 9.41 (bs, 1H).

EXAMPLE 33

N-Cyano-N'-(7-phenoxyheptyl)-N"-4-pyridylguanidine

By following the procedure of Example 1, but substituting N-(7-phenoxyheptyl)-N'-4-pyridylthiourea for N-(3-phenoxypropyl)-N'-4-pyridylthiourea, the desired compound was obtained.

The compound was further purified by a recrystallisation from water/acetone/ether.

$^1$H NMR (DMSO) δ: 1.25–1.62 (m, 8H), 1.71 (m, 2H), 3.27 (bt, 2H), 3.94 (t, 2H), 6.90 (m, 3H), 7.10–7.33 (m, 4H), 7.84 (bs, 1H), 8.37 (d, 2H), 9.40 (bs, 1H).

EXAMPLE 34

N-Cyano-N'-(4-phenylaminobutyl)-N"-4-pyridylquanidine

By following the procedure of Example 1, but substituting N-(4-phenylaminobutyl)-N'-4-pyridylthiourea for N-(3-phenoxypropyl)-N'-4-pyridylthiourea, the desired compound was obtained.

The compound was further purified by flash chromatography (silica gel, eluent $CH_2Cl_2$/MeOH 90:10 followed by 80:20) and crystallized from ether.

$^1$H NMR (DMSO) δ: 1.60 (m, 4H), 3.02 (q, 2H), 3.33 (m, 2H), 5.53 (t, 1H), 6.50 (t, 1H), 6.55 (d, 2H), 7.05 (t, 2H), 7.21 (d, 2H), 7.87 (bs, 1H), 8.38 (d, 2H), 9.42 (bs, 1H).

EXAMPLE 35

N-Cyano-N'-(6-phenylthiohexyl)-N"-4-pyridylquanidine

By following the procedure of Example 1, but substituting N-(6-phenylthiohexyl)-N'-4-pyridylthiourea for N-(3-phenoxypropyl)-N'-4-pyridylthiourea, the desired compound was obtained.

The compound was further purified by a recrystallisation from water/acetone/ether.

$^1$H NMR (DMSO) δ: 1.20–1.65 (m, 8H), 2.95 (t, 2H), 3.25 (bs, 2H), 7.18 (m, 3H), 7.31 (m, 4H), 7.83 (bs, 1H), 8.38 (d, 2H), 9.40 (bs, 1H).

EXAMPLE 36

N-Cyano-N'-(4-phenylthiobutyl)-N"-4-pyridylquanidine, S-oxide

N-Cyano-N'-(4-phenylthiobutyl)-N"-4-pyridylguanidine (0.50 g) was suspended in chloroform (20 ml) and cooled on ice. m-Chloroperbenzoic acid (0.41 g) in chloroform (5 ml) was added during 20 minutes. The reaction mixture was stirred overnight at 5° C. The reaction mixture was washed twice with icecold saturated sodium hydrogen carbonate and with water. The organic phase was dried with sodium sulphate and concentrated. The product was crystallized from ether.

$^1$H NMR (DMSO) δ: 1.40–1.75 (m, 4H), 2.80 (m, 1H), 2.99 (m, 1H), 3.26 (q, 2H), 7.19 (bs, 2H), 7.50–7.95 (m, 6H), 8.39 (bs, 2H), 9.35 (bs, 1H).

EXAMPLE 37

N-(6-p-Chlorophenoxyhexyl)-N'-cyano-N"-4-pyridylquanidine, N-oxide

N-(6-p-Chlorophenoxyhexyl)-N'-cyano-N"-4-pyridylguanidine (2.0 g) was suspended in methylene chloride (15 ml) and cooled on ice. m-Chloroperbenzoic acid (1.21 g) in methylene chloride (20 ml) was added during 7 minutes. After two hours more m-chloroperbenzoic acid (1.21 g) in methylene chloride (20 ml) was added during 15 minutes. After a reaction time of 6 hours the product was purified by flash chromatography (silica gel, eluent 0–30% MeOH and 1% $NH_3$(aq) in $CH_2Cl_2$) and crystallized from ether.

$^1$H NMR (DMSO) δ: 1.38 (m, 4H), 1.54 (m, 2H), 1.70 (m, 2H), 3.26 (q, 2H), 3.95 (t, 2H), 6.94 (d, 2H), 7.30 (m, 4H), 7.77 (t, 1H), 8.10 (d, 2H), 9.39 (bs, 1H).

EXAMPLE 38

N-(6-p-Chlorophenoxyhexyl)-N'-cyano-N"-(3,5-dibromo-4-pyridyl) quanidine and N-(3-bromo-4-pyridyl)-N'-(6-p-chlorophenoxyhexyl)-N"-cyanoguanidine N-(6-p-Chlorophenoxyhexyl)-N'-cyano-N"-4-pyridylguanidine (2.0 g) was dissolved in DMF (20 ml) and cooled on ice. Sodium hydride (60%, 0.26 g) was added and after 10 minutes N-bromosuccinimide (1.16 g) was added. Addition of sodium hydride and N-bromosuccinimide was repeated after 1.5 hours at 0° C. The reaction mixture was left at 5° C. overnight. Water and methylene chloride were added and the phases were separated. The water phase was extracted twice with methylene chloride. The collected organic phases were dried with sodium sulphate and concentrated. After flash chromatography (silica gel, eluent 0–6% MeOH and 1% $NH_3$(aq) in $CH_2Cl_2$) the two products were crystallized from ether.

N-(6-p-Chlorophenoxyhexyl)-N'-cyano-N"-(3,5-dibromo-4-pyridyl) guanidine:

$^1$H NMR (DMSO) δ: 1.25–1.62 (m, 6H), 1.71 (m, 2H), 3.17 (bs, 2H), 3.95 (t, 2H), 6.94 (d, 2H), 7.30 (d, 2H), 7.30 (bs, 1H), 8.79 (s, 2H), 9.29 (bs, 1H).

N-(3-bromo-4-pyridyl)-N'-(6-p-chlorophenoxyhexyl)-N"-cyanoguanidine:

$^1$H NMR (DMSO) δ: 1.38 (m, 4H), 1.55 (m, 2H), 1.71 (m, 2H), 3.25 (q, 2H), 3.95 (t, 2H), 6.94 (d, 2H), 7.31 (m, 3H), 7.76 (bt, 1H), 8.43 (bs, 1H), 8.68 (bs, 1H), 9.04 (bs, 1H).

EXAMPLE 39

N-Cyano-N'-(6-p-hydroxyphenoxyhexyl)-N"-4-pyridylguanidine

N-(6-p-Benzyloxyphenoxyhexyl)-N'-cyano-N"-4-pyridylguanidine (1.0 g) was dissolved in ethanol (30 ml) and hydrogenated at 1 atm using 5% Pd on charcoal (100 mg) as the catalyst. After flash chromatography (silica gel, eluent 0–15% MeOH and 0.5% $NH_3$(aq) in $CH_2Cl_2$) the product was crystallized from ether.

$^1$H NMR (DMSO) δ: 1.37 (m, 4H), 1.55 (m, 2H), 1.67 (m, 2H), 3.28 (q, 2H), 3.84 (t, 2H), 6.65 (d, 2H), 6.72 (d, 2H), 7.22 (bs, 2H), 7.85 (bt, 1H), 8.38 (bd, 2H), 8.87 (s, 1H), 9.37 (bs, 1H).

EXAMPLE 40

N-Cyano-N'-(6-phenylaminohexyl)-N"-4-pyridylquanidine

By following the procedure of Example 1, but substituting N-(6-phenylaminohexyl)-N'-4-pyridylthiourea for N-(3-phenoxypropyl)-N'-4-pyridylthiourea, the desired compound was obtained. The compound was further purified by a recrystallisation from water/acetone.

Mp. 136° C.

¹H NMR (DMSO) δ: 1.35 (m, 4H), 1.54 (m, 4H), 2.97 (q, 2H), 3.30 (bt, 2H), 5.48 (t, 1H), 6.49 (t, 1H), 6.53 (d, 2H), 7.05 (t, 2H), 7.20 (bd, 2H), 7.84 (bs, 1H), 8.37 (d, 2H), 9.41 (bs, 1H).

EXAMPLE 41

N-Cyano-N'-(8-phenoxyoctyl)-N"-4-pyridylquanidine

By following the procedure of Example 1, but substituting N-(8-phenoxyoctyl)-N'-4-pyridylthiourea for N-(3-phenoxypropyl)-N'4-pyridylthiourea, the desired compound was obtained. The compound was further purified by a recrystallisation from water/acetone.

Mp. 79° C.

¹H NMR (DMSO) δ: 1.25–1.48 (m, 8H), 1.53 (m, 2H), 1.70 (m, 2H), 3.27 (bt, 2H), 3.94 (t, 2H), 6.91 (d, 3H), 7.21 (bd, 2H), 7.27 (t, 2H), 7.83 (bs, 1H), 8.38 (d, 2H), 9.39 (bs, 1H).

EXAMPLE 42

N-Cyano-N'-(6-p-nitrophenoxyhexyl)-N"-4-pyridylquanidine

By following the procedure of Example 1, but substituting N-(6-p-nitrophenoxyhexyl)-N'-4-pyridylthiourea for N-(3-phenoxypropyl)-N'-4-pyridylthiourea, the desired compound was obtained.

Mp. 156°–161° C.

¹H NMR (DMSO) δ: 1.30–1.50 (m, 4H), 1.56 (m, 2H), 1.76 (m, 2H), 3.28 (bt, 2H), 4.12 (t, 2H), 7.13 (d, 2H), 7.21 (bd, 2H), 7.85 (bs, 1H), 8.20 (d, 2H), 8.38 (d, 2H), 9.41 (bs, 1H).

EXAMPLE 43

N-(6-p-Chlorophenoxyhexyl)-N'-cyano-N"-4-pyridylquanidine

By following the procedure of Example 1, but substituting N-(6-p-chlorophenoxyhexyl)-N'-4-pyridylthiourea for N-(3-phenoxypropyl)-N'-4-pyridylthiourea, the desired compound was obtained.

¹H NMR (DMSO) δ: 1.27–1.50 (m, 4H), 1.55 (m, 2H), 1.73 (m, 2H), 3.28 (q, 2H), 3.95 (t, 2H), 6.94 (d, 2H), 7.22 (bd, 2H), 7.30 (d, 2H), 7.86 (t, 1H), 8.38 (d, 2H), 9.45 (bs, 1H).

EXAMPLE 44

N-Cyano-N'-(6-p-methoxyphenoxyhexyl)-N"-4-pyridylquanidine

By following the procedure of Example 1, but substituting N-(6-p-methoxyphenoxyhexyl)-N'-4-pyridylthiourea for N-(3-phenoxypropyl)-N'-4-pyridylthiourea, the desired compound was obtained.

¹H NMR (DMSO) δ: 1.30–1.50 (m, 4H), 1.55 (m, 2H), 1.69 (m, 2H), 3.28 (t, 2H), 3.69 (s, 3H), 3.88 (t, 2H), 6.84 (s, 4H), 7.20 (bd, 2H), 7.81 (bs, 1H), 8.37 (d, 2H), 9.40 (bs, 1H).

EXAMPLE 45

N-Cyano-N'-(6-m-nitrophenoxyhexyl)-N"-4-pyridylquanidine

By following the procedure of Example 1, but substituting N-(6-m-nitrophenoxyhexyl)-N'-4-pyridylthiourea for N-(3-phenoxypropyl)-N'-4-pyridylthiourea, the desired compound was obtained.

The product was purified by flash chromatography (silica gel, eluent 0–10% MeOH in CH₂Cl₂) and crystallized from ether.

Mp. 142° C.

¹H NMR (DMSO) δ: 1.30–1.50 (m, 4H), 1.57 (m, 2H), 1.76 (m, 2H), 3.29 (bs, 2H), 4.10 (t, 2H), 7.22 (bd, 2H), 7.40 (m, 1H), 7.57 (t, 1H), 7.69 (t, 1H), 7.79 (m, 1H), 7.84 (bs, 1H), 8.38 (d, 2H), 9.39 (bs, 1H).

EXAMPLE 46

N-Cyano-N'-(6-p-nitrophenylthiohexyl)-N"-4-pyridylquanidine

By following the procedure of Example 1, but substituting N-(6-p-nitrophenylthiohexyl)-N'-4-pyridylthiourea for N-(3-phenoxypropyl)-N'-4-pyridylthiourea, the desired compound was obtained.

¹H NMR (DMSO) δ: 1.25–1.60 (m, 6H), 1.66 (m, 2H), 3.12 (t, 2H), 3.26 (bs, 2H), 7.21 (bs, 2H), 7.49 (d, 2H), 7.84 (bs, 1H), 8.13 (d, 2H), 8.38 (d, 2H), 9.40 (bs, 1H).

EXAMPLE 47

N-(5-Bromo-3-pyridyl)-N'-cyano-N"-(6-phenoxyhexyl)-quanidine

A mixture of N-(5-bromo-3-pyridyl)-N'-6-phenoxyhexylurea (3.39 g), triphenylphosphine (3.33 g), triethylamine (1.57 ml), and carbon tetrachloride (1.5 ml) in dry methylene chloride (56 ml) was heated under reflux in an argon atmosphere for 16 hours. The mixture was evaporated in vacuo, and the residue was triturated with ether (6×50 ml) and filtered. The filtrate was evaporated in vacuo to give the crude carbodiimide which was reacted with cyanamide (509 mg) after the addition of N-ethyl diisopropylamine (0.5 ml), ether (25 ml), and chloroform (20 ml). The mixture was stirred in an argon atmosphere for 24 hours.

The reaction mixture was purified by flash chromatography (silica gel, eluent 50–66% ethyl acetate in pentane) to afford an almost pure compound. Crystallisation from a mixture of acetone and water yielded the pure compound.

Mp. 98°–100° C.

¹H NMR (DMSO) δ: 1.30–1.50 (m, 4H), 1.62(m, 2H), 1.73 (m,2H), 3.36 (bt, 2H), 3.96 (t, 2H), 6.85–6.95 (m, 4H), 7.27 (m, 2H), 8.32 (t, 1H), 8.76 (d, 1H), 8.93 (d, 1H), 9.38 (bs, 1H).

EXAMPLE 48

N-(7-p-Chlorophenoxyheptyl)-N'-cyano-N"-4-pyridylquanidine 7-p-Chlorophenoxyheptylamine (2.0 g), S-methyl N-cyano-N'-4-pyridylisothiourea (1.54 g), dimethylaminopyridine (25 mg), triethylamine (1.16 ml) and pyridine (7 ml) were mixed and stirred for two weeks at room temperature.

The compound was isolated by precipitation with ether followed by filtration. The compound was further purified by extraction with water.

¹N NMR (DMSO) δ: 1.25–1.48 (m, 6H), 1.54 (m, 2H), 1.70 (m, 2H), 3.28 (q, 2H), 3.94 (t, 2H), 6.94 (d, 2H), 7.22 (bd, 2H), 7.31 (d, 2H), 7.86 (bt, 1H), 8.39 (d, 2H), 9.29 (bs, 1H).

EXAMPLE 49

N-(6-m-Chlorophenoxyhexyl)-N'-cyano-N"-4-pyridylguanidine

By following the procedure of Example 48, but substituting 6-m-chlorophenoxyhexylamine for 7-p-chlorophenoxyheptylamine, the desired compound was obtained.

The compound was further purified by recrystallisation from chloroform.

$^1$H NMR (DMSO) δ: 1.30–1.50 (m, 4H), 1.54 (m, 2H), 1.71 (m, 2H), 3.28 (q, 2H), 3.98 (t, 2H), 6.90 (m, 1H), 6.95 (m, 2H), 7.22 (bd, 2H), 7.29 (t, 1H), 7.84 (bt, 1H), 8.38 (bd, 2H), 9.38 (bs, 1H).

EXAMPLE 50

N-Cyano-N'-(6-m-methoxyphenoxyhexyl)-N"-4-pyridylguanidine

By following the procedure of Example 48, but substituting 6-m-methoxyhenoxyhexylamine for 7-p-chlorophenoxyheptylamine, the desired compound was obtained.

The compound was isolated by flash chromatography (silica gel, eluent $CH_2Cl_2$/MeOH/$NH_3$(aq) 95:5:0.5) and further purified by trituration with a mixture of methylene chloride, ether and ethyl acetate (2:2:1).

Mp. 138°–139° C.

$^1$H NMR (DMSO) δ: 1.30–1.50 (m, 4H), 1.56 (m, 2H), 1.70 (m, 2H), 3.28 (q, 2H), 3.72 (s, 3H), 3.93 (t, 2H), 6.50 (m, 3H), 7.16 (t, 1H), 7.22 (bd, 2H), 7.84 (bt, 1H), 8.38 (bd, 2H), 9.39 (bs, 1H).

EXAMPLE 51

N-Cyano-N'-(6-o-nitrophenoxyhexyl)-N"-4-pyridyl guanidine

By following the procedure of Example 48, but substituting 6-o-nitrophenoxyhexylamine for 7-p-chlorophenoxyheptylamine, the desired compound was obtained.

The reaction mixture was evaporated in vacuo. The compound was isolated by flash chromatography (silica gel, eluent $CH_2Cl_2$/MeOH/$NH_3$ (aq) 98:2:0.2)

Mp. 162°–163° C.

$^1$H NMR (DMSO) δ: 1.30–1.50 (m, 4H), 1.55 (m, 2H), 1.75 (m, 2H), 3.28 (q, 2H), 4.15 (t, 2H), 7.10 (t, 1H), 7.22 (bd, 2H), 7.35 (d, 1H), 7.63 (m, 1H), 7.85 (m, 2H), 8.38 (bd, 2H), 9.39 (bs, 1H).

EXAMPLE 52

N-Cyano-N'-4-pyridyl-N"-(6-(2,4,5-trichlorophenoxy)hexyl)guanidine

By following the procedure of Example 48, but substituting 6-(2,4,5-trichlorophenoxy) hexylamine for 7-p-chlorophenoxyheptylamine, the desired compound was obtained.

The compound was isolated by precipitation with ether followed by filtration. The compound was further purified by flash chromatography (silica gel, eluent $CH_2Cl_2$/MeOH/$NH_3$(aq) 98:2:0.2).

$^1$H NMR (DMSO) δ: 1.30–1.50 (m, 4H), 1.55 (m, 2H), 1.75 (m, 2H), 3.26 (q, 2H), 4.09 (t, 2H), 7.22 (bs, 2H), 7.44 (d, 1H), 7.78 (d, 1H), 7.84 (bt, 1H), 8.38 (bd, 2H), 9.38 (bs, 1H).

EXAMPLE 53

N-Cyano-N'-(6-o-methoxyphenoxyhexyl)-N"-4-pyridylguanidine

By following the procedure of Example 48, but substituting 6-o-methoxyphenoxyhexylamine for 7-p-chlorophenoxyheptylamine, the desired compound was obtained.

The compound was isolated by precipitation with ether followed by filtration. The compound was further purified by flash chromatography (silica gel, eluent $CH_2Cl_2$/MeOH/$NH_3$ (aq) 98:2:0.2).

$^1$H NMR (DMSO) δ: 1.30–1.50 (m, 4H), 1.56 (m, 2H), 1.72 (m, 2H), 3.38 (q, 2H), 3.74 (s, 3H), 3.95 (t, 2H), 6.85–7.00 (m, 4H), 7.22 (bs, 2H), 7.85 (bt, 1H), 8.38 (bd, 2H), 9.37 (bs, 1H).

EXAMPLE 54

N-(6-o-Chlorophenoxyhexyl)-N'-cyano-N"-4-pyridylguanidine

By following the procedure of Example 48, but substituting 6-o-chlorophenoxyhexylamine for 7-p-chlorophenoxyheptylamine, the desired compound was obtained.

The reaction mixture was evaporated in vacuo and the compound was purified by flash chromatography (silica gel, eluent $CH_2Cl_2$/MeOH/$NH_3$ (aq) 98:2:0.2).

Mp. 141°–142° C.

$^1$H NMR (DMSO) δ: 1.30–1.50 (m, 4H), 1.56 (m, 2H), 1.76 (m, 2H), 3.28 (bq, 2H), 4.05 (t, 2H), 6.93 (m, 1H), 7.12 (dd, 1H), 7.22 (bd, 2H), 7.28 (m, 1H), 7.40 (dd, 1H), 7.85 (bt, 1H), 8.38 (bd, 2H), 9.39 (bs, 1H).

EXAMPLE 55

N-Cyano-N'-(6-(2,3,4,5,6-pentachlorophenoxy) hexyl)-N"-4-pyridylguanidine

By following the procedure of Example 48, but substituting 6-(2,3,4,5,6-pentachlorophenoxy) hexylamine for 7-p-chlorophenoxyheptylamine, the desired compound was obtained.

The compound was isolated by filtration and washed with ether. The compound was further purified by a recrystallisation from chloroform/methanol 1:1.

$^1$H NMR (DMSO) δ: 1.35–1.65 (m, 6H), 1.80 (m, 2H), 3.29 (q, 2H), 4.03 (t, 2H), 7.23 (bs, 2H), 7.85 (bt, 1H), 8.38 (bd, 2H), 9.38 (bs, 1H).

EXAMPLE 56

N-Cyano-N'-(6-(3,4-methylenedioxyphenoxy)hexyl)-N"-4-pyridylguanidine

By following the procedure of Example 48, but substituting 6-(3,4-methylenedioxyphenoxy)hexylamine for 7-p-chlorophenoxyheptylamine, the desired compound was obtained.

The reaction mixture was evaporated in vacuo and the compound was isolated by flash chromatography (silica gel, eluent $CH_2Cl_2$/MeOH/$NH_3$(aq) 95:5:0.5). The compound was further purified by a recrystallisation from methanol.

$^1$H NMR (DMSO) δ: 1.38 (m, 4H), 1.55 (m, 2H), 1.68 (m, 2H), 3.27 (q, 2H), 3.87 (t, 2H), 5.94 (s, 2H), 6.34 (dd, 1H), 6.60 (d, 1H), 6.78 (d, 1H), 7.22 (bs, 2H), 7.84 (bt, 1H), 8.38 (bd, 2H), 9.36 (bs, 1H).

EXAMPLE 57

N-Cyano-N'-(6-(3,4-dichlorophenoxy)hexyl)-N"-4-pyridylguanidine

By following the procedure of Example 48, but substituting 6-(3,4-dichlorophenoxy)hexylamine for 7-p-chlorophenoxyheptylamine, the desired compound was obtained.

The compound was isolated by filtration and washed with ether.

Mp. 154°–155° C.

$^1$H NMR (DMSO) δ: 1.37 (m, 4H), 1.53 (m, 2H), 1.71 (m, 2H), 3.28 (q, 2H), 3.99 (t, 2H), 6.94 (dd, 1H), 7.21 (m, 4H), 7.49 (d, 1H), 7.84 (bt, 1H), 8.38 (bd, 2H), 9.36 (bs, 1H).

EXAMPLE 58

N-Cyano-N'-(6-(2,4-dichlorophenoxy)hexyl)-N"-4-pyridylguanidine

By following the procedure of Example 48, but substituting 6-(2,4-dichlorophenoxy)hexylamine for 7-p-chlorophenoxyheptylamine, the desired compound was obtained.

The compound was isolated by filtration and washed with ether. The compound was further purified by a recrystallisation from chloroform.

Mp. 128°–130° C.

$^1$H NMR (DMSO) δ: 1.30–1.50 (m, 4H), 1.56 (m, 2H), 1.74 (m, 2H), 3.28 (q, 2H), 4.05 (t, 2H), 7.16 (d, 1H), 7.22 (bs, 2H), 7.35 (dd, 1H), 7.54 (d, 1H), 7.84 (bt, 1H), 8.38 (bd, 2H), 9.36 (bs, 1H).

EXAMPLE 59

N-(6-(4-Chloro-3-methylphenoxy)hexyl)-N'-cyano-N"-4-pyridylquanidine

By following the procedure of Example 48, but substituting 6-(4-Chloro-3-methylphenoxy)hexylamine for 7-p-chlorophenoxyheptylamine, the desired compound was obtained.

The compound was isolated by filtration and washed with ether.

Mp. 144°–145° C.

$^1$H NMR (DMSO) δ: 1.30–1.50 (m, 4H), 1.56 (m, 2H), 1.71 (m, 2H), 2.28 (s, 3H), 3.28 (q, 2H), 3.93 (t, 2H), 6.77 (dd, 1H), 6.93 (d, 1H), 7.23 (bs, 2H), 7.27 (d, 1H), 7.84 (bt, 1H), 8.38 (bd, 2H), 9.39 (bs, 1H).

EXAMPLE 60

N-Cyano-N'-(6-(2,5-dichlorophenoxy)hexyl)-N"-4-pyridylguanidine

By following the procedure of Example 48, but substituting 6-(2,5-dichlorophenoxy) hexylamine for 7-p-chlorophenoxyheptylamine, the desired compound was obtained.

The compound was isolated by filtration and washed with ether. The compound was further purified by a recrystallisation from chloroform/methanol 1:1.

Mp. 179°–180° C.

$^1$H NMR (DMSO) δ: 1.30–1.50 (m, 4H), 1.56 (m, 2H), 1.75 (m, 2H), 3.28 (q, 2H), 4.08 (t, 2H), 7.00 (dd, 1H), 7.23 (bd, 3H), 7.43 (d, 1H), 7.84 (bt, 1H), 8.38 (bd, 2H), 9.38 (s, 1H).

EXAMPLE 61

N-Cyano-N'-4-pyridyl-N"-(6-(2,4,6-trichlorophenoxy)hexyl)quanidine

By following the procedure of Example 48, but substituting 6-(2,4,6-trichlorophenoxy)hexylamine for 7-p-chlorophenoxyheptylamine, the desired compound was obtained.

The compound was isolated by filtration and washed with ether.

Mp. 144°–145° C.

$^1$H NMR (DMSO) δ: 1.30–1.65 (m, 6H), 1.76 (m, 2H), 3.28 (q, 2H), 3.97 (t, 2H), 7.22 (bs, 2H), 7.68 (s, 2H), 7.84 (bt, 1H), 8.38 (bd, 2H), 9.35 (bs, 1H).

EXAMPLE 62

N-Cyano-N'-(6-p-fluorophenoxyhexyl)-N"-4-pyridylquanidine

By following the procedure of Example 48, but substituting 6-p-fluorophenoxyhexylamine for 7-p-chlorophenoxyheptylamine, the desired compound was obtained.

The compound was isolated by filtration and washed with ether.

Mp. 164°–165° C.

$^1$H NMR (DMSO) δ: 1.40 (m, 4H), 1.56 (m, 2H), 1.71 (m, 2H), 3.28 (q, 2H), 3.93 (t, 2H), 6.92 (m, 2H), 7.10 (t, 2H), 7.22 (bs, 2H), 7.84 (bt, 1H), 8.38 (bd, 2H), 9.38 (bs, 1H).

EXAMPLE 63

N-(6-p-Bromophenoxyhexyl)-N'-cyano-N"-4-pyridylguanidine

By following the procedure of Example 48, but substituting 6-p-bromophenoxyhexylamine for 7-p-chlorophenoxyheptylamine, the desired compound was obtained.

The compound was isolated by filtration and washed with ether.

Mp. 161°–163° C.

$^1$H NMR (DMSO) δ: 1.41 (m, 4H), 1.56 (m, 2H), 1.71 (m, 2H), 3.28 (bt, 2H), 3.94 (t, 2H), 6.99 (d, 2H), 7.21 (bd, 2H), 7.42 (d, 2H), 7.84 (bs, 1H), 8.38 (bd, 2H), 9.38 (bs, 1H).

EXAMPLE 64

N-Cyano-N'-(6-(2,3-dichlorophenoxy)hexyl)-N"-4-pyridylquanidine

By following the procedure of Example 48, but substituting 6-(2,3-dichlorophenoxy) hexylamine for 7-p-chlorophenoxyheptylamine, the desired compound was obtained.

The compound was isolated by filtration and washed with ether.

Mp. 155°–156° C.

$^1$H NMR (DMSO) δ: 1.30–1.50 (m, 4H), 1.55 (m, 2H), 1.76 (m, 2H), 3.28 (q, 2H), 4.08 (t, 2H), 7.10–7.35 (m, 5H), 7.84 (bt, 1H), 8.39 (bd, 2H), 9.36 (bs, 1H).

EXAMPLE 65

N-Cyano-N'-(6-(3,5-dimethoxyphenoxy)hexyl)-N"-4-pyridylquanidine

By following the procedure of Example 48, but substituting 6-(3,5-dimethoxyphenoxy) hexylamine for 7-p-chlorophenoxyheptylamine, the desired compound was obtained.

The reaction mixture was evaporated in vacuo and the compound was isolated by flash chromatography (silica gel, eluent CH$_2$Cl$_2$/MeOH/NH$_3$ (aq) 95:5:0.5). The compound was further purified by a recrystallisation from chloroform.

$^1$H NMR (DMSO) δ: 1.40 (m, 4H), 1.55 (m, 2H), 1.70 (m, 2H), 3.27 (q, 2H), 3.70 (s, 6H), 3.91 (t, 2H), 6.08 (s, 3H), 7.22 (bd, 2H), 7.84 (bt, 1H), 8.38 (bd, 2H), 9.37 (bs, 1H).

EXAMPLE 66

N-Cyano-N'-(6-p-methylphenoxyhexyl)-N''-4-pyridylquanidine

By following the procedure of Example 48, but substituting 6-p-methylphenoxyhexylamine for 7-p-chlorophenoxyheptylamine, the desired compound was obtained.

The compound was isolated by filtration and washed with ether.

Mp. 167°–169° C.

$^1$H NMR (DMSO) δ: 1.39 (m, 4H), 1.55 (m, 2H), 1.70 (m, 2H), 2.22 (s, 3H), 3.28 (q, 2H), 3.90 (t, 2H), 6.79 (d, 2H), 7.06 (d, 2H), 7.22 (bs, 2H), 7.84 (bt, 1H), 8.38 (bd, 2H), 9.37 (bs, 1H).

EXAMPLE 67

N-((Z)-(S)-6-p-Chlorophenoxy-1-hydroxymethylhex-2-enyl)-N'-cyano-N''-4-pyridylquanidine By following the procedure of Example 48, but substituting (Z)-(S)-6-p-chlorophenoxy-1-hydroxymethylhex-2-enyl hexylamine for 7-p-chlorophenoxyheptylamine, the desired compound was obtained.

The reaction mixture was evaporated in vacuo and the compound was purified by flash chromatography (silica gel, eluent CH$_2$Cl$_2$/MeOH/NH$_3$ (aq) 98:2:0.2).

$^1$H NMR (DMSO) δ: 1.70–2.05 (m, 3H), 2.25–2.50 (m, 2H), 3.54 (dd, 1H), 3.95 (m, 3H), 4.86 (m, 1H), 5.52 (m, 1H), 5.76 (m, 1H), 6.85 (d, 2H), 7.25 (m, 3H), 7.35 (d, 2H), 7.65 (s, 1H), 8.49 (d, 2H).

EXAMPLE 68

N-Cyano-N'-(6-m-hydroxyphenoxyhexyl)-N''-4-pyridylquanidine

By following the procedure of Example 48, but substituting 6-m-hydroxyphenoxyhexylamine for 7-p-chlorophenoxyheptylamine, the desired compound was obtained.

The compound was evaporated in vacuo and further purified by trituration with tetrahydrofurane.

Mp. 136°–142° C.

$^1$H NMR (DMSO) δ: 1.38 (m, 4H), 1.55 (m, 2H), 1.67 (m, 2H), 3.27 (q, 2H), 3.88 (t, 2H), 6.32 (m, 3H), 7.02 (t, 1H), 7.22 (bd, 2H), 7.86 (t, 1H), 8.38 (bd, 2H), 9.36 (bs, 2H).

What we claim is:

1. A compound N-(6-p-Chlorophenoxyhexyl)-N'-cyano-N''-4-pyridylguanidine, and pharmaceutically acceptable, non-toxic salts and N-oxides thereof.

2. A method of treating a host to obtain a serotonin (5HT) antagonist effect therein which comprises administering to a host in need of such treatment, an effective amount of a compound according to claim 1.

3. A method according to claim 2 for the treatment of asthma, allergy, CNS disorders, or cancer.

4. A pharmaceutical composition comprising, as active ingredient, a compound according to claim 1 and a pharmaceutically acceptable carrier therefor.

5. A method of treating a host to obtain a serotonin (5HT) antagonist effect therein which comprises administering to a host in need of such treatment, an effective amount of a compound according to claim 4.

6. A method according to claim 5 for the treatment of asthma, allergy, CNS disorders, or cancer.

7. A method of treatment which comprises administering to a host in need of treatment of cancer, an effective amount of a compound of the formula (I)

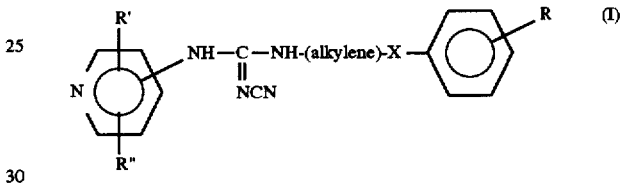

or their tautomeric forms, the attachment to the pyridine ring being in the 3- or 4-position, in which R', R'' are the same or different and stand for hydrogen, halogen, or trifluoromethyl, hydroxy, C$_1$–C$_4$ alkyl or alkoxy, nitro, or cyano groups; alkylene stands for a straight or branched C$_1$–C$_8$ carbon chain, which may be substituted by hydroxy or halogen, nitro or cyano groups; X stands for oxygen, for —S(O)$_n$— where n stands for an integer from 0 to 2, or for

where R$_1$ is hydrogen or C$_1$–C$_4$ alkyl; R stands for hydrogen or for one or more C$_1$–C$_4$ alkyl or alkoxy, hydroxy, halogen, trifluoromethyl, cyano, carboxamido, sulfamoyl or nitro radicals; their N-oxides; or pharmaceutically acceptable, non-toxic salts thereof.

8. A method of cancer treatment according to claim 7, wherein the compound is selected from the group consisting of N-Cyano-N'-(3-phenoxypropyl)-N''-4-pyridylguanidine, N-Cyano-N'-(4-phenoxybutyl)-N''-4-pyridylguanidine, N-Cyano-N'-(5-phenoxypentyl)-N''-4-pyridylguanidine, N-(6-p-Chlorophenoxyhexyl)-N'-cyano-N''-4-pyridylguanidine, and pharmaceutically acceptable, non-toxic salts and N-oxides thereof.

* * * * *